United States Patent [19]

Wanamaker et al.

[11] Patent Number: 5,117,837
[45] Date of Patent: Jun. 2, 1992

[54] BLOOD DRAWING APPARATUS

[75] Inventors: Thomas Wanamaker, R.R. 2, Box 619, Smithville, Mo. 64089; Teryl K. Rouse, Kansas City, Mo.

[73] Assignee: Thomas Wanamaker, Smithville, Mo.

[21] Appl. No.: 702,321

[22] Filed: May 20, 1991

[51] Int. Cl.$^5$ .............................................. A61B 5/00
[52] U.S. Cl. ................................... 128/763; 128/770; 604/240
[58] Field of Search ............... 128/760, 763, 764, 770; 604/240

[56] References Cited

U.S. PATENT DOCUMENTS

| | | | |
|---|---|---|---|
| 4,841,985 | 6/1989 | Wanamaker | 128/763 |
| 4,907,600 | 3/1990 | Spencer | 128/764 |
| 4,984,580 | 1/1991 | Wanamaker | 128/763 |
| 5,046,508 | 9/1991 | Weissler | 128/763 |

FOREIGN PATENT DOCUMENTS 8905118  6/1989  World Int. Prop. O. .......... 128/763

Primary Examiner—Max Hindenburg
Attorney, Agent, or Firm—Michael Yakimo, Jr.

[57] ABSTRACT

A blood collection system comprising a needle assembly, an evacuated collection tube and a holder for said tube. A housing at the end of said holder receives an adaptor therein. A conventional cannula assembly is threaded into the adaptor such that the rear cannula end extends into the collection tube with the front cannula end extending forwardly for venipuncture. A locking assembly traversing the housing includes first and second slide locks with apertures therein. The slide locks have a first biased position in which portions of the adaptor are engaged by the rims of the apertures to hold the cannula within the housing. Upon user manipulation of the locks, the slide locks are moved to disengage the rims from the adaptor. The latter movement causes release of the adaptor with cannula assembly from the housing allowing for cannula disposal subsequent to use without user handling.

17 Claims, 2 Drawing Sheets

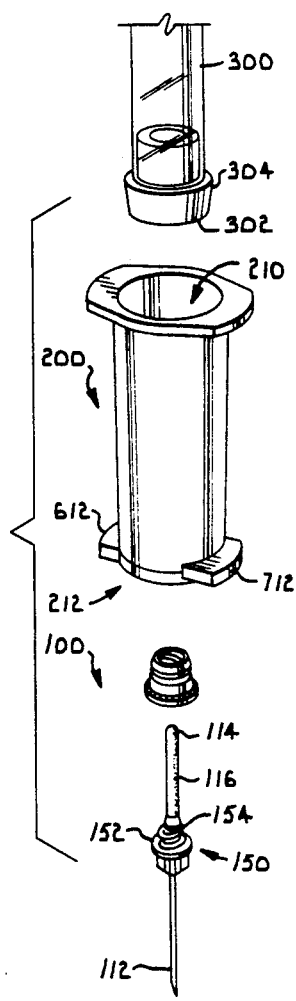
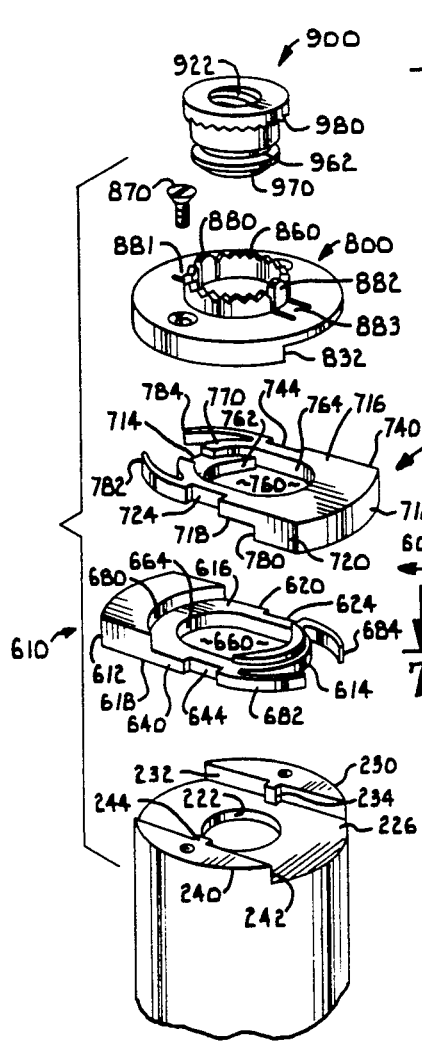
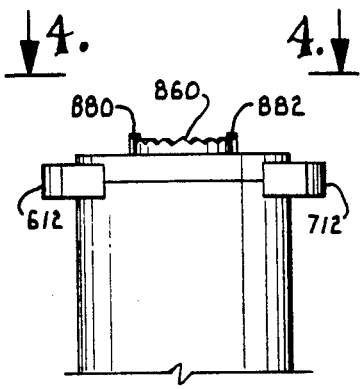
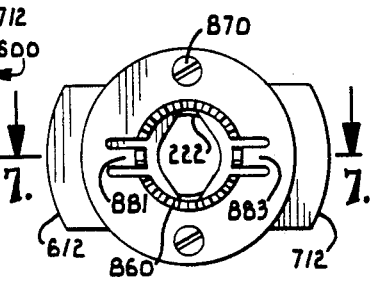
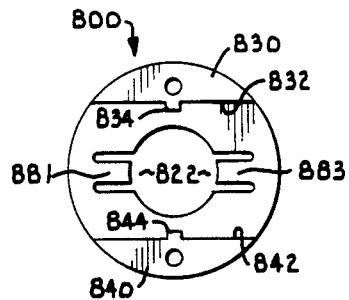
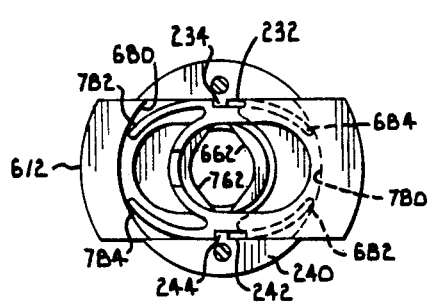
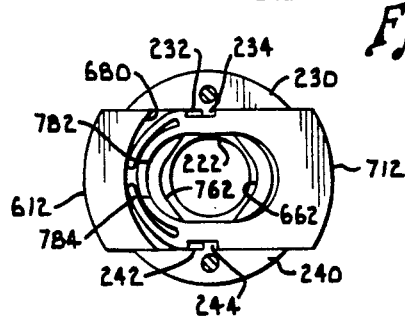
Fig. 1.
Fig. 2.
Fig. 3.
Fig. 4.
Fig. 10.
Fig. 5.
Fig. 6.

BLOOD DRAWING APPARATUS

BACKGROUND OF THE INVENTION

This invention pertains to a blood sampling device and more particularly to apparatus which reduces the possibility of contamination by diseased blood to the user.

The analysis of the patient's blood is an important diagnostic tool. Blood is drawn from the patient by the use of various syringe-type apparatus. Blood collection devices utilize a needle/cannula inserted into the vein of the patient, i.e. venipuncture, so as to draw the blood through the needle and into an associated collection reservoir. In light of the AIDS problems, attention has been directed to the risk of contamination of the blood drawer/user due to contact with the blood of a diseased patient. Contamination may occur either through the user being punctured by a user needle upon its removal from the blood collection device and/or the splashing of the blood onto the user during such removal.

Various blood collection devices are common in the art. Devices addressing the above problems have also been the subject of prior patents such as those shown in my U.S. Pat. Nos. 4,841,985 and 4,984,580. The basic device generally comprises a needle holder, a needle/cannula assembly and evacuated blood collection tube. The needle assembly, as engaged in the needle holder, presents a front end for puncturing the vein of the patient and a rear end for insertion into an evacuated collection tube contained within the holder. The evacuated tube causes the blood to be drawn from the patient, via the front needle end, and discharged into the collection tube via the rear needle end. As the disposal of the used cannula/needle assembly requires manual handling, the possibility of skin puncture and/or diseased blood splashing onto the user arises after use.

I have invented another needle holder/needle assembly which eliminates the need for the user to manually handle the used needle assembly subsequent to blood purging. An adaptor for a common cannula/needle assembly is inserted into the housing of the holder. The cannula hub is threaded into the adaptor prior to removal of the protective needle cap. The adaptor and cannula threaded therein are held in place by a pair of sliding locks interposed in the housing. Each lock has a slot therein presenting a locking rim. Each rim engages the adaptor so as to maintain the same within the housing. The locking position of the locking rims is maintained by a pair of resilient, bias arms at the front end of each lock which bear against a surface on the opposite lock. The tendency of the bias arms to return to a normal position urges each of the sliding locks into opposed directions and the locking rims into engagement with the housed adaptor. Subsequent to blood withdrawal, the user compresses the sliding locks so as to disengage the locking rims for discharge of the adaptor and associated cannula from the needle holder. The cannula may thus be directed into a waste receptacle for subsequent disposal. Thus, the user need not manually handle the needle assembly subsequent to use.

It is therefor a primary object of this invention to provide for an improved blood collection device which reduces the risk of contamination to users.

Another general object of this invention is to provide for a blood collection device, as aforesaid, which particularly reduces the risk of contamination upon disposal of the utilized needle/cannula assembly.

Still another general object of this invention is to provide for a blood collection device, as aforesaid, which precludes the need for the user to manually handle the needle assembly after use.

Another object of this invention is to provide a blood collection device, as aforesaid, which utilizes a needle assembly releasably engageable with a needle holder.

A further object of this invention is to provide a blood collection device, as aforesaid, which utilizes a bias on the needle assembly to urge removal of the needle assembly from the associated needle holder.

Other objects and advantages of this invention will become apparent from the following description taken in connection with the accompanying drawings, wherein is set forth by way of illustration and example, a now preferred embodiment of this invention.

BRIEF DESCRIPTION OF THE DRAWINGS

FIG. 1 is an exploded view of the elements of the blood drawing system;

FIG. 2 is an exploded view, on an enlarged scale, of the holder, housing and locking assemblies of the blood drawing system with the cannula adaptor displaced therefrom;

FIG. 3 is a side elevation view of the holder prior to insertion of the adaptor therein;

FIG. 4 is a top plan view, taken along line 4—4 in FIG. 3, illustrating the housing assembly and interposed slide locks as presented to the user prior to insertion of the adaptor therein;

FIG. 5 is a top plan view, similar to FIG. 4, with the lid of the housing assembly being removed to show the underlying slide locks of the locking assembly in a normal position with the locking rims of each slide lock subtending the central aperture in the holder;

FIG. 6 is a top plan view, similar to FIGS. 4 and 5, illustrating the slide locks of the locking assembly in a compressed position such that the locking rims of each slide lock are outside the central aperture in the holder;

FIG. 10 is a plan view illustrating the underside of the lid of the housing assembly.

DESCRIPTION OF THE PREFERRED EMBODIMENT

Figure 9:
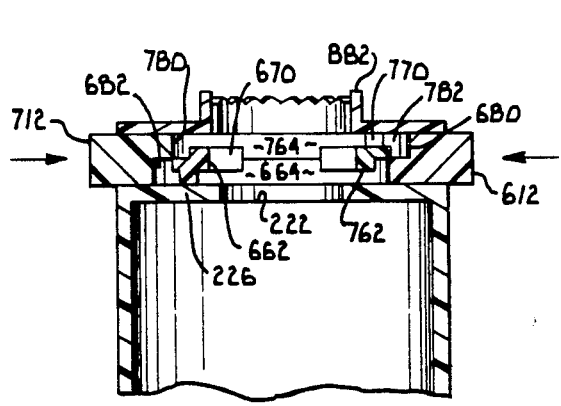
FIG. 9 is a sectional elevation view, similar to that shown in FIGS. 7 and 8, illustrating the compressed position of the slide locks allowing for release of the slide locks from the adaptor and the needle therein.

Turning more particularly to the drawings, FIG. 1 illustrates my now preferred blood collection device as generally comprising a needle assembly 100, including adaptor 900, a needle holder 200 and an evacuated sample collection tube 300.

The needle assembly 100 also referred to as a cannula structure, generally comprises a front needle end 112 for venipuncture and a covered 116 rear end 114 for insertion through a membrane 302 of the stopper 304 of tube 300. A removable cap (not shown) encloses the front end 112 of the needle prior to use. An intermediate hub 150 surrounds the needle and includes a stop ring 152 and threads 154.

The holder 200 is cylindrical in configuration for reception of the evacuated collection tube 300 through the proximal or input end 210. The distal end 212, relative to the user, presents an end wall 226 with a central aperture 222 therein. The aperture 222 is bounded by a pair of parallel flanges 230, 240 thereon. Each flange 230, 240 presents a vertical wall 232, 242 having a medially located stop 234, 244 thereon. These vertical walls 232, 242, as located on opposed sides of the central aperture 222, present rails and cooperate with the end wall 226 so as to define a track 250 for a slidable lock 610 of the locking assembly 600.

The locking assembly 600 is interposed between the end wall 226 and housing cover 800 and comprises first 610 and second 710 slide locks as shown in FIG. 2. Slide lock 610 includes a pair of end walls 612, 614 a top wall 616, bottom wall 618 and a pair of opposed side walls 620, 640 having notches 624, 644 therein. The side walls 620, 640 are laterally displaced to allow for insertion of the lock 610 between the side walls 232, 242 of track 250. Upon such insertion the stops 234, 244 are positioned within the respective notches 624, 644. As such, the bottom wall 618 of slide lock 610 is slidable along the course of track 250 and atop the end wall 226 with the extent of the slidable movement being limited by the stops 234, 244 engaging the limits of the notches 624, 644.

The slide lock 610 further has a central oval aperture 660 having a configuration larger than that of the central aperture 222. The aperture 660 presents a wall having a rim 664 with the leading portion of the rim 664 being designated as a locking rim 662.

Extending from the top wall 616 and adjacent end wall 612 is a curved bearing surface or brake wall 680. A pair of bias arms 682, 684 extend from the side walls and past the opposed end wall 614 of slide lock 610. A locking flange 670 extends from top wall 616 adjacent the locking rim 662 and cooperates with the locking rim 662 to lock and/or stabilize adaptor 900 in a manner to be subsequently described.

A second slide lock 710 is similar in configuration to slide lock 610 and includes a pair of end walls 712, 714, top wall 716, bottom wall 718 and a pair of opposed side walls 720, 740 having notches 724, 744 therein. The lock 710 has a central aperture 760 similar to aperture 660 presenting a rim 764 with a leading portion of rim being designated as a locking rim 762. Extending from a top wall 716 is a curved bearing surface or brake wall 780. A pair of bias arms 782, 784 extending from the side walls 720, 740 and past the opposed end wall 712. A locking flange 770 extends from top wall 716 adjacent the locking rim 762 and cooperates with locking rim 762 to lock and/or stabilize adaptor 900 in a manner to be subsequently described. Upon placement of the slide lock 710 atop lock 610 bias arms 782, 784 contact brake wall 680 of lock 610. Concurrently, the bias arm 682, 684 of lock 610 contact the adjacent brake wall 780 of lock 710. It is noted that the flanges 670, 770 extend through the apertures 760, 660 of the opposite slide locks 710, 610. Thus, the bottom wall 718 of the lock 710 rests on top wall 616 of lock 610 and such walls 718, 610 are slidable therebetween.

Figure 8:
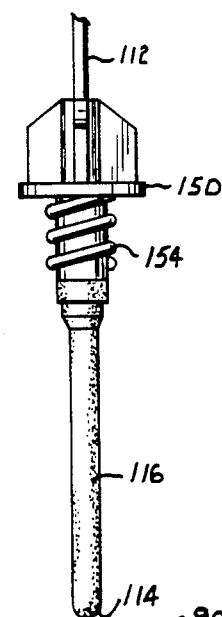
FIG. 8 is a sectional elevation view, similar to that of FIG. 7, illustrating the engagement position of the slide locks with the adaptor and the needle within the adaptor.
Figure 8:
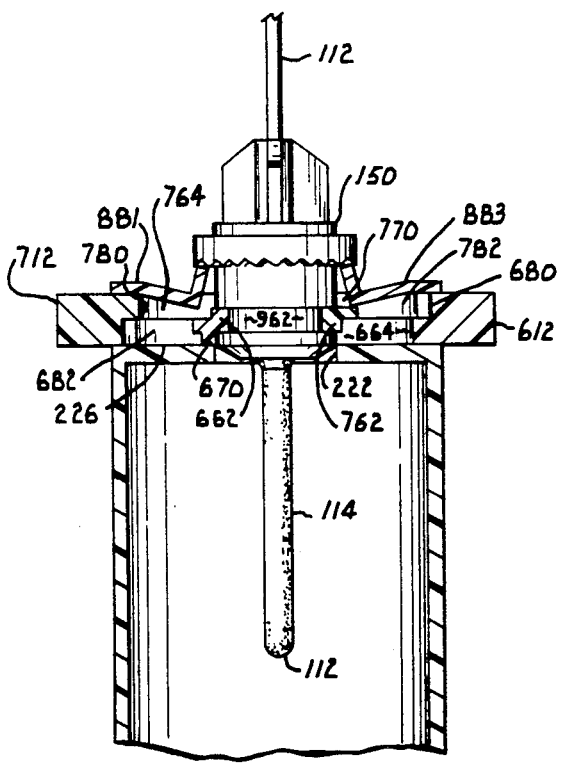
Figure 7:
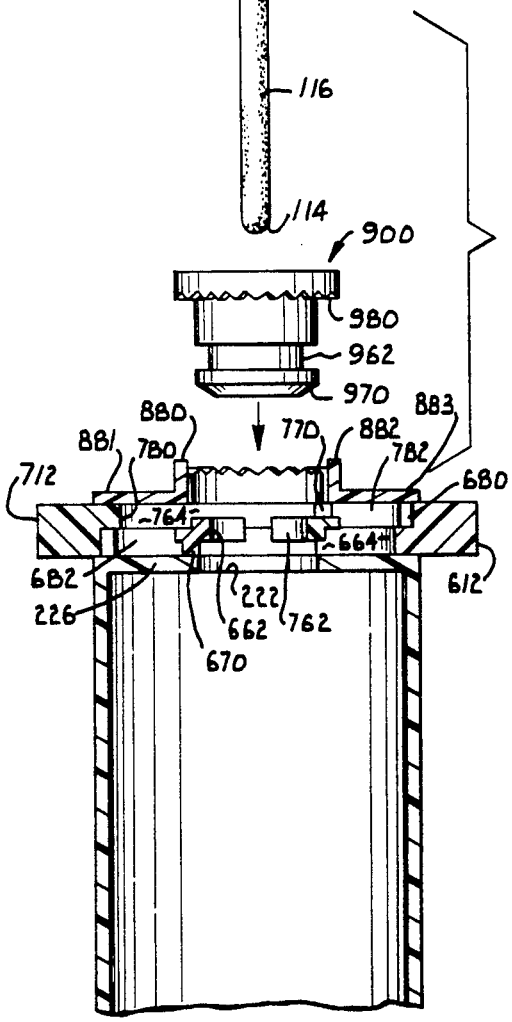
FIG. 7 is a sectional elevation view, on an enlarged scale and rotated approximately 180° from the FIG. 2 position, illustrating the normal position of the slide locks prior to movement of the adaptor element into the holder housing with the needle assembly displaced therefrom.

It is noted that the walls of the slide locks have been directionally defined as to the orientation of the device in FIG. 2 for purposes of illustration and not limitation. Please note that FIGS. 7-9 illustrate the device in FIG. 2 in a non-exploded position and rotated approximately 180° from the FIGS. 1-6 orientation.

The relative normal position of the slide locks 610, 710 of locking assembly is best shown in FIG. 5. As such, the respective resilient bias arms 682, 684, 782, 784 have not yet been compressed against brake walls/bearing surfaces 680, 780 but are at their normal extended position. At this position the resilient arms in their non-compressed position contact the brake walls 780, 680 of the other slide locks 710, 610. As such the locking rims 662, 762 obstruct or subtend a portion of the central aperture 222 in end wall 226.

Positioned atop the locks 610, 710 is a housing cover 800. As shown in FIG. 10 the cover has flanges 830, 840 with side walls 832, 842 and stops 834, 844 preferably congruent to flanges 230, 240 and stop lugs 234, 244. The lid 800 further includes a central aperture 822 as defined by a cylindrical boss 850 having serrated edges 860 at the free end thereof. Upon placement of lid 800 atop flanges 230, 240 with screw fasteners 870, the stops 834, 844 are positioned within notches 724, 744 of the slide lock 710. Accordingly, the slidable movement of slide lock 710 is delimited by the stops 834, 844 within their respective notches 724, 744. The sidewalls 832, 842 of flanges 830, 840 thus likewise act as rails for slide lock 710 and cooperate with the aligned rails/sidwalls 232, 242 to form track 250.

Upon screw 870 fastening, central aperture 822 of cover 800 is aligned with aperture 222. The fastened cover 800 cooperates with the underlying holder 200 to present a housing having aligned apertures 222, 822 for insertion of an adaptor 900 and associated needle assembly 100 therein. As shown in FIG. 4, the slide plates 610, 710 are in their normal position such that the locking rims/leading edges 662, 762 of the slide plates 610, 710 subtends the aperture 822 of lid 800 as well as the aligned aperture 222 in end wall 226. Such a position is achieved as the resilient bias arms 682, 684, 782, 784 are allowed to expand to their normal non-compressed position as best shown in FIG. 5.

Adaptor 900 has a central threaded aperture 922, an annular locking notch 962 and a forward frustro-conical edge 970. A crown 980 has a serrated rim 982 and is of a diameter congruent to the serrated rim 860 of the boss housing 850 in lid 800.

Upon insertion of the adaptor 900 into the aperture 822, the leading frustro-conical/bevelled edge 970 bears against the locking rims 662, 762 and forces the associated slide locks into opposed slidable movement along the track 250 towards the outside of holder 200. This action compresses the respective bias arms 682, 684, 782, 784 against the adjacent braking walls 780, 680. Upon further insertion of the adaptor 900, the annular locking slot 962 becomes aligned with the locking rims/edges 662, 762. This relationship allows the compressed bias arms 682, 684, 782, 784 to return from the FIG. 6 position towards their FIG. 5 position such that locking rims/edges 662, 762 seat within the locking slot 962. Also the locking flanges 670, 770 bear against portions of the adaptor 900 above and below the slot 962 to offer additional stability to the seated adaptor. Accordingly, the adaptor 900 is maintained within the holder as shown in FIG. 8.

Subsequently, the rear end 114 of the cannula 100 is inserted through the adaptor 900 aperture 922. The threaded 154 hub 150 is screwed into the adaptor 900 threads 954. The stop 150 of needle 100 abuts the top planar surface 992 of crown 990 when threading is complete. The engagement of the serrations 982 of crown 980 with serrations 860 of the boss 850 precludes the adaptor 900 from further rotation. Concurrently, the rim 982 of crown 980 bears against bias arms 880, 882 within the boss 850. Such bearing depresses the arms 880, 882 and associated base 881, 883 as best shown in FIG. 8.

When threaded the rear portion 114 of the needle extends into the holder as best shown in FIG. 8. Upon insertion of the evacuated tube 300 into the holder the cover 116 will be peeled back so that the exposed rear end 114 of the needle will pierce the membrane 302 of rubber stopper 304 and extend into the collection tube. The cap surrounding the front needle 112 can then be removed. Upon insertion of the front needle end 112 into the vein, the blood will be drawn through the bore of the needle and discharged from end 114 into the tube 300. The tube 300 may then be removed from holder 200.

Subsequent to use the user presses the end walls 612, 712 of the respective slide locks 610, 710 extending outside the housing. This action moves the slide locks 610, 710 so as to compress the respective bias arms 782, 784, 682, 684 of the slide locks 710, 610 against the adjacent respective braking walls 680, 780. This compression displaces the seated locking rims 662, 762 and flanges 670, 770 from the annular locking notch 962 and side walls of the adaptor 900. Moreover, edges 662, 762 are moved outside the aligned apertures 222, 822. Such displacement releases the adaptor 900 and needle assembly 100 from its locked position for direction towards a waste receptacle. The release of the adaptor 900 from its locked position is assisted by the return of the depressed bases 881, 883 of bias arms 880, 882 from their depressed position. Upon adaptor 900 release the lid 800 bases 881, 883 return to their normal position as shown in FIGS. 7 and 9.

Upon release of the end walls by the user the compressed bias arms 682, 684, 782, 784, as shown in FIG. 6, will be allowed to return to their FIG. 5 position. This action causes the slide locks 610, 710 to move through the track 250 in opposed directions. The lugs 234, 244, 834, 844 in the respective notches 624, 644, 724, 744 delimits the slidable movement of such locks 610, 710 in such opposed directions.

It is to be understood that while a certain form of this invention has been illustrated and described, it is not limited thereto, except in so far as such limitations are included in the following claims and allowable functional equivalents thereof.

Having thus described the invention, what is claimed as new and desired to be secured by Letters Patent is:

1. A blood drawing system for use with a double ended cannula assembly open at both ends and having a bore for passage of fluid therethrough comprising:
    a holder having means therein for releasably mounting the cannula assembly with one end extending forwardly of said holder for venipuncture and the other end extending reardwardly for coupling with a collection container, said mounting means comprising:
        housing means at one end of said holder for receiving a portion of said cannula therein with said one cannula end extending forwardly of said housing means in said venipuncture position and said other end extending rearwardly for said coupling with said collection container;
        user-operable locking means for releasably engaging said cannula assembly to said housing means upon insertion of said cannula in said housing means, said locking means comprising:
            first and second slide locks, each having an aperture therein presenting a rim for engagement with a portion of said cannula assembly;
            means for mounting said slide locks in back and forth motion relative to said cannula;
            means for biasing said slide locks towards a first position wherein said rims engage a portion of said cannula upon insertion in said housing means to maintain said cannula in place;
            means for moving said slide locks to a second position to disengage said rims from said cannula and release said cannula from said housing means.

2. The device as claimed in claim 1 wherein said housing means comprises:
    an end wall at one end of said holder;
    an aperture in said end wall;
    a boss extending from said cover and having a free end;
    an aperture in said boss;
    means for fastening said cove to said end wall with said boss aperture being aligned with said end wall aperture for reception of said cannula therein.

3. The device as claimed in claim 2 wherein said mounting means further comprises:
    track means interposed between said end wall and said cover for presenting a course of movement for said slide locks.

4. The device as claimed in claim 3 wherein said track means comprises:
    a first flange extending from said end wall and presenting a rail generally spanning said end wall at a position displaced from said end wall aperture;
    a second flange extending from said end wall and presenting a second rail generally spanning said end wall at a position displaced from said end wall aperture, said first and second rails being generally parallel for presenting a track for movement of said slide locks therebetween.

5. The device as claimed in claim 4 wherein each slide lock comprises:
    a top wall;
    a bottom wall with said aperture extending between said top and bottom walls;
    a first end wall;
    a second end wall;
    a pair of laterally displaced side walls configured to fit between said rails of said track, said slide locks being positioned one atop the other and between said rails.

6. The device as claimed in claim 5 further comprising:
    a notch in at least one of said side walls of each slide lock;
    a lug along said rail and positioned within said notch of an adjacent slide lock;
    said lug bearing against a portion of said notch during said slide lock movement in a manner to delimit said movement of said lock along said track means.

7. The device as claimed in claim 6 further comprising:

a notch in at least one of said side walls of said slide lock adjacent said cover;

a lug in said cover and positioned in said notch upon said fastening of said cover to said end wall;

said lug bearing against a portion of said notch during said slide lock movement in a manner to delimit said movement of said slide lock along said track.

8. The device as claimed in claim 2 wherein a portion of said rim of each slide lock aperture subtends an arc of said aligned end wall and cover apertures of said housing means in said biased first position.

9. The device as claimed in claim 8 wherein a ion of said rims are outside said aligned end wall and cover apertures at said second position.

10. The device as claimed in claim 2 wherein said bias means comprises:

a resilient arm extending from a first end of each slide lock and having compressed and normal modes;

a bearing surface on the other of said slide locks for contact with said resilient arm of the other of said slide locks;

each resilient arm being compressed against said surface at said second position, said compressed arms urging each of said slide locks into said first position upon return to said normal mode.

11. The device as claimed in claim 10 wherein said moving means comprises:

an end wall of each of said slide locks extending from said holder, whereupon user movement of said end walls one towards the other moves said slide locks to said second position.

12. The device as claimed in claim 2 wherein said cannula assembly comprises:

an adaptor having a central aperture for insertion into said boss and in alignment with said end wall and cover apertures;

an intermediate hub interposed between said cannula ends;

means in said adaptor for engaging said hub with said cannula end extending rearwardly from said hub for said coupling with said collection container and said other cannula end extending forwardly from said hub for said venipuncture.

13. The device as claimed in claim 12 wherein said adaptor includes an annular notch for engagement with said portion of said rims therein at said first position.

14. The device as claimed in claim 13 wherein said adaptor further comprises:

a generally cone-shaped end presenting a bevelled surface, said bevelled surface urging said rims at said first position away from said aligned end wall and cover apertures to allow insertion of said adaptor into said boss, said bias means urging said rims into said second position and into said annular notch subsequent to said insertion of said adaptor.

15. The device as claimed in claim 14 wherein said adaptor further comprises:

a crown presenting an edge;

a plurality of serrations about said edge;

said boss free end having a plurality of serrations for mating with said adaptor serrations to preclude rotation of said adaptor in said boss.

16. The device as claimed in claim 15 wherein said boss further comprises a bias arm engaging said adaptor upon said insertion and depressing said cover from a normal position, said cover moving from said compressed to said normal position upon said movement of said slide locks to said second position, said cover movement assisting said cannula release.

17. A blood drawing system for use with a double ended cannula assembly open at both ends and having a bore for passage of fluid therethrough comprising:

a holder having means therein for releasably mounting the cannula assembly with one end extending forwardly of said holder for venipuncture and the other end extending rearwardly for coupling with a collection container, said mounting means comprising:

housing means at one end of said holder and including a central aperture for receiving a portion of said cannula therein with said one cannula end extending forwardly of said housing means in said venipuncture position and said other end extending rearwardly for said coupling with said collection container;

user-operable locking means for releasably engaging said cannula assembly to said housing means upon insertion of said cannula in said housing means, said locking means comprising:

at least one slide lock having an aperture therein presenting a rim for engagement with a portion of said cannula assembly, said lock aperture having an area at least congruent with said central aperture;

means for mounting said slide lock in back and forth motion through said housing means;

means for biasing said slide lock towards a first position in which said rim subtends said central aperture to provide for said engagement of said cannula and maintain said cannula in said housing means;

means for moving said slide lock to a second position to generally align said central aperture with said slide lock aperture to disengage said rim and release said cannula from said housing means.

* * * * *

UNITED STATES PATENT AND TRADEMARK OFFICE
CERTIFICATE OF CORRECTION

PATENT NO. : 5,117,837
DATED : June 2, 1992
INVENTOR(S) : Thomas Wanamaker et al It is certified that error appears in the above—identified patent and that said Letters Patent is hereby corrected as shown below:

Column 3, line 53, delete "extending" and substitute --extend--.

Column 3, line 60, delete "arm" and substitute --arms--.

Column 4, line 28, delete "sidwalls" and substitute --sidewalls--.

Column 7, line 12, delete "ion" and substitute --portion--.

Signed and Sealed this

Third Day of August, 1993

Attest:

MICHAEL K. KIRK

*Attesting Officer*      *Acting Commissioner of Patents and Trademarks*